United States Patent [19]

Hoerle

[11] 4,086,139

[45] Apr. 25, 1978

[54] DIFFERENTIAL INACTIVATION OF AMYLASE IN AMYLASE-PROTEASE MIXTURES

[75] Inventor: Raymond D. Hoerle, Highland Park, Ill.

[73] Assignee: GB Fermentation Industries Inc., Kingstree, S.C.

[21] Appl. No.: 675,385

[22] Filed: Apr. 9, 1976

[51] Int. Cl.² .............................................. C07G 7/02
[52] U.S. Cl. .................................. 195/66 R; 195/65
[58] Field of Search ............... 195/66 R, 121, 122, 195/123, 65, 62; 426/20

[56] References Cited

U.S. PATENT DOCUMENTS

| 1,892,247 | 12/1932 | Neugebauer | 195/66 R |
|---|---|---|---|
| 2,262,138 | 11/1941 | Frey et al. | 426/20 |
| 2,647,854 | 4/1953 | Pfannmuller et al. | 195/31 R |
| 2,683,682 | 7/1954 | Miller et al. | 195/66 R |
| 3,578,462 | 5/1971 | Smerak et al. | 426/63 X |
| 3,709,790 | 1/1973 | Beuk et al. | 195/66 R |
| 3,755,085 | 8/1973 | Tivin et al. | 195/68 |
| 3,795,586 | 3/1974 | Ziffer | 195/68 |

OTHER PUBLICATIONS

Waku et al., Chemical Abstract, 78: 107533(p), (1973).
Maltsev et al., Chemical Abstract, vol. 51: 11414b (1957).

*Primary Examiner*—Lionel M. Shapiro
*Attorney, Agent, or Firm*—Hammond & Littell

[57] ABSTRACT

Use of hypochlorite and chlorite ions to differentially inactivate amylase in protease-amylase mixtures, and product produced thereby.

19 Claims, No Drawings

DIFFERENTIAL INACTIVATION OF AMYLASE IN AMYLASE-PROTEASE MIXTURES

BACKGROUND OF THE INVENTION

This invention relates to proteolytic enzyme compositions which are substantially free of amylase activity, and to a method for preparing such compositions. In particular, this invention relates to proteolytic enzyme compositions which are prepared by a unique method for differentially or selectively inactivating amylase in mixtures of protease and amylase.

Proteolytic enzyme compositions are derived by well known techniques from bacterial and fungal cultures as well as animal organs such as the pancreas. In particlar, the production of protease-containing enzyme mixtures from bacterial sources is well known. Usually, amylase enzymes are co-produced during the growth of the microorganism. For certain purposes, it is desired to provide a protease-containing preparation which is substantially free of any amylase enzyme. For example, applications which require enzymic action on the protein phase of a substance without affecting its amylase content would desirably employ a protease enzyme preparation free of amylolytic activity. Thus, in the treatment of soy flour with protease, for certain purposes it is desirable to use an amylase-free enzyme preparation.

Various known methods of purifying and isolating enzymes include fractional precipitation with inorganic salts such as sodium and ammonium sulfates or polymeric precipitants; organic solvents such as alcohols and ketones; ion exchange chromatography; selective absorption and elution with calcium phosphate gels; separation on columns of CMC or DEAE cellulose; Sephadex gel filtration; differential heat inactivation at varying pH's; isoelectric precipitation; ultrafiltration; and ultracentrifrifugation. Further description of conventional techniques for enzyme purification and isolation is found in *Process Biochemistry*, August 1973, page 9 et seq. and references cited therein.

A particularly efficacious method for removing undesirable enzyme activity from crude compositions comprises treating the composition to inactivate the contaminant enzyme while leaving the desired activity substantially intact. Hence, although the inactive contaminant is present in the composition it is as effectively neutralized as if it has been physically removed. Inactivation in this context is an irreversible inactivation rather than mere inhibition. Thus, upon removal or dilution of the inactivating agent there is no reappearance of the inactivated enzyme activity. The cost of these inactivation methods is considerably less than purification techniques which requires expensive reagents and multiple processing and separation steps. Such an inactivation method is disclosed in U.S. Pat. No. 2,683,682, where the pH of a proteinase and alpha-amylase preparation is adjusted to differentially inactivate either proteinase or alpha-amylase.

With the foregoing prior art in mind, it is an object of this invention to provide proteolytic enzyme compositions which have been rendered substantially free of amylase activity without the need for lengthy separatory steps or the use of expensive reagents.

It is a further object of this invention to provide a method for treating mixtures of proteolytic and amylolytic enzymes, particularly those derived from bacterial and animal sources, to obtain proteolytic enzyme compositions which are substantially free of amylase activity.

It is an additional object of this invention to provide a method for inactivating amylase in protease compositions while simultaneously destroying any microorganisms present.

It is a further object of this invention to provide proteolytic enzyme compositions substantially free of amylase activity which are stable upon storage.

These and other objects of the invention will be apparent to those skilled in the art from a consideration of this specification taken in its entirety.

SUMMARY OF THE INVENTION

I have discovered that the protease in a mixed protease-amylase enzyme composition can be freed of its amylase activity by treating the composition with an oxidizing agent selected from the group consisting of chlorite and hypochlorite ions.

The ions are added to the enzyme mixture in an amount sufficient to inactivate the amylase to a greater degree than the protease. This will generally entail substantially inactivating the amylase while leaving the protease at substantially its original activity in the untreated composition. Since the ions are largely consumed by the composition during the inactivation of amylase and since the inactivated amylase is merely an enzymatically innocuous protein, there is no need for any separation or purification steps following treatment with the ions. The composition after treatment is storage stable.

An additional advantage of the process is that the ions will reduce or eliminate the microorganism population in the compositions. These populations might otherwise eventually result in either spoilage of the compositions or adverse effects on products made by the use of the compositions.

It is known to combine oxidizing or bleaching agents, including hypochlorite ion, with enzymes. For example, see U.S. Pat. Nos. 2,262,138, 3,709,790, 3,755,085 and 3,795,586 as well as "Chemical Abstracts" 78:107533 p(1973). Barium peroxide has been employed to inactivate amylases as well as proteinases (U.S. Pat. No. 2,647,854). Further, it is generally known to reduce the microbial contamination of materials and surfaces by treating them with hypochlorite. However, none of these references teach that amylase in protease-amylase mixtures can be differentially inactivated. In fact, the "Chemical Abstracts" reference would suggest the opposite.

DESCRIPTION OF THE PREFERRED EMBODIMENTS

A suitable oxidizing agent for inactivating the amylase is hypochlorite ion ($ClO^-$). It may be provided by hypochlorous acid or an alkali metal salt of hypochlorous acid, e.g., sodium, potassium, calcium or magnesium hypochlorite. Similarly, chlorite ion ($ClO_2^-$) is directly available as chlorous acid or an alkali metal salt thereof. As used herein, the suffix "ite" is intended to refer to an ion donated by either the acid or the salt. Generally, either ion will be used alone in aqueous solution. However, mixtures of the two ions can be employed. Further, they can be provided by an in situ reaction which will yield either or both ions from precursors added to the composition. The reaction and its starting material must, of course, not be detrimental to the protease. Furthermore, the reaction and starting materials should preferably be unhazardous. Thus, for example, it is not preferred to introduce the anhydride of hypochlorite, chlorine monoxide ($Cl_2O$) into an aqueous enzyme composition to form hypochlorite in situ. Rather, it is preferred to add sodium hypochlorite in dilute aqueous solution to the enzyme preparation. A readily available dilute aqueous solution of sodium hypochlorite which contains 5.25% sodium hypochlorite and 94.75% inert materials is sold under the trademark Clorox ®.

Suitable enzyme compositions which may be differentially inactivated according to the process of this invention include those obtained from bacteria and animals. Animal-derived compositions are those obtained from animals which have discrete organs or fluids capable of recovery as an enzyme source. An example of such an organ is the pancreas, a rich source of digestive enzymes including protease and amylase. A pancreatic enzyme composition suitable for treatment according to the process of this invention is pancreatin, a well-known material containing lipase, esterase, protease and amylase.

Amylase-containing proteases from a great variety of bacteria are suitable for use in the process of this invention. Particularly preferred are the proteases from *Bacillus subtilis* and *Bacillus licheniformis*.

The effectiveness or extent of differential inactivation of amylase in protease compositions can depend upon many factors. For example, the ratio of the concentration of either or both ions to the amount of protein in the mixed protease-amylase composition, the dilution of the composition, and the pH, temperature and time of contacting the ions with the composition can effect the result obtained. Such factors can be readily balanced by the ordinary worker in this art so as to inactivate amylase to the desired degree while substantially maintaining the protease activity. It is usually desired to inactivate at least about 80% of the amylase while reducing the protease activity less than about 20%. According to the process of this invention it is commonly possible to achieve a reduction in amylase activity of more than 95% while simultaneously reducing the protease activity less than 5%. The inactivation can be followed by any of the well-known assays for proteolytic and amylolytic activity.

Desirable results are obtained by the process of this invention over a wide range of weight ratios of enzyme composition to added ions. The composition need only be treated with sufficient ions to substantially inactivate the composition's amylase activity while leaving the protease activity essentially unchanged. Illustratively, from about 0.1% to about 5% of ion by weight, based on the ambient air dry weight of powdered enzyme composition, provides satisfactory results. It is preferred to use from about 0.2% to about 0.5% hypochlorite ion or from about 0.2% to 2% chlorite ion. The most preferred concentrations of either ion used separately are about 0.30% hypochlorite and about 0.35% chlorite. Usually, for any given quantity of chlorite somewhat less hypochlorite may be employed. In summary, the quantity of ions used is not critical. Too little will result in relatively high residual amylase activities, although this might be desirable in some uses for the treated composition, while too much is a waste of reagent.

The enzyme compositions to be treated may be substantially or essentially cell-free solutions such as fermentation broth filtrates, crude animal organ extracts or solutions of dried fermentation broth filtrates. The compositions may contain not only a fermentation broth but also the cells of the microorganism used alone or in combination with a plurality of other species to produce the mixed protease-amylase compositions. Further, any of the foregoing compositions may contain contaminant cells. These cells will be killed by the treatment, an additional advantage of the inventive process. Thus, it is unnecessary to employ a separate step in the process of this invention to render the composition free of living cells. It should be noted that a large number of cells will consume so much of the ions that supplementation of the added ions may be necessary to ensure the desired inactivation of amylase.

Suitable sources of mixed protease-amylase enzyme systems which can be used as starting materials in the present invention are known and can be obtained by microbial fermentation using well-known fermentation methods such as those generally described in Kirk-Othmer, *Encyclopedia of Chemical Technology*, 8, 173–230, and references cited therein. In particular, the use of bacterial sources for producing mixed proteolytic and amylolytic enzyme systems by fermentation is described in U.S. Pat. No. 2,530,210.

An especially suitable source of a protease-containing enzyme composition is *Bacillus subtilis*. This microorganism is a species of bacteria which is widely distributed, spore-forming, aerobic and catalase-positive. It is classified in *Bergey's Manual of Determinative Bacteriology*, pp. 613–621 (7th ed. 1957), published by Williams and Wilkins Co., Baltimore, Md., and in *Aerobic Spore Forming Bacteria*, Agricultural Monograph No. 16, U.S. Department of Agriculture. This microorganism is readily available to the public in view of its wide distribution in nature. Numerous cultures of this microorganism also are available in public depositories affording permanence of the deposit where they are readily accessible to the public. One such example has been deposited in the American Type Culture Collection, Rockville, Md., and has been designated ATCC 6051a. Another example of this microorganism is the culture deposited with the U.S. Department of Agriculture, Agricultural Research Service, Northern Utilization Research and Development Division, Peoria, Ill., under accession number NRRL B-3411. Still other examples will be apparent to the person skilled in the art by reference to various well-known public depositories of microorganisms throughout the world.

The enzyme composition may be dry, in solution, or a slurry when contacted with the oxidizing agent. The concentration of composition in solution is not critical. A range of from about 5% to about 75% solids by weight in water or buffer is generally employed, with about 20% being preferred. The concentration selected will largely depend upon whatever processing techniques are to be used prior to or after the treatment. For example, a low solids content is generally characteristic of fermentation broths and these can be treated by the process of the invention without further processing. On the other hand if a concentrated end product is desired then the composition solution may be dewatered to the appropriate degree before treatment.

Any pH of treatment may be selected which does not adversely affect the protease activity. The protease activity as a function of pH will vary depending upon the source of the enzyme composition. As a practical matter most crude compositions from either bacterial or animal sources contain a plurality of proteases, each active over a different pH range. It is the distribution of these proteases that determines the pH activity range for the enzymes. Thus, where within a pH range of about 3 to about 10 an enzyme will exhibit the best protease activity depends upon the distribution of proteases in the composition. When employing the *B. subtilis* enzyme mixture a range of from about 5.8 to about 7 is preferred and about 6.3 is optimal. Adjustment of the enzyme mixture to the desired pH, if necessary, can be conveniently done by addition of a suitable amount of dilute acid or alkali.

Neither the temperature nor time of ion treatment are critical, although the temperature should not be so high as to inactivate the protease. Solutions at from slightly above freezing to about 60° C may be illustratively treated for about several minutes to three hours. Generally, longer treatment times are needed with lower temperatures and concentrations of ion. It is preferred to treat the solutions from about 1 hour and 15 minutes at about room temperature. The selection of these parameters is largely a matter of economics.

Following the treatment with the oxidizing agent, the solution may be processed in any conventional manner to ready the product for further use. It is generally lyophilized or spray dried, processes which also remove residual chlorite or hypochlorite ion.

The following examples are intended to further illustrate the invention, although it will be understood that the invention is not limited to these specific examples.

EXAMPLE 1

An alkaline protease composition from *B. subtilis*, sold by the Wallerstein Co. under the name Alkaline Protease was dissolved in tap water to a concentration of 20% by weight based on the room dry weight of the composition. There was no effort made to remove insoluble material, although this could be readily done if desired. The pH of this solution was 6.3. Sufficient amounts of sodium hypochlorite and sodium chlorite aqueous solution were added with mixing to 26 g. aliquots of the protease solution to yield a variety of sodium hypochlorite and chlorite concentrations based on the room dry weight of the enzyme composition. These concentrations are expressed in Table I as percentages. The varying increments of inactivating ion solution were equalized by the addition of water. The addition of the inactivating ions did not significantly alter the initial pH of the enzyme solution. The ions remained in contact with the enzyme solution for about 1¼ hr. The solution was then assayed for protease and amylase activity. Results are shown in Table I.

TABLE I
EFFECT OF CHLORITE AND HYPOCHLORITE ADDITION ON PROTEASE AND AMYLASE ACTIVITY

| Ion Salt Added | % Ion salt | Amylase activity[1] | % loss | Protease activity[2] | % loss |
|---|---|---|---|---|---|
|  | 0 | 282 | — | 40,300 | — |
| sodium chlorite | 0.152 | 151 | 47 | 40,800 | 0 |
|  | 0.304 | 14 | 95 | 40,800 | 0 |
|  | 0.486 | 3 | 99 | 39,900 | 1 |
|  | 1.94 | 2 | 99 | 37,200 | 8 |
|  | 0 | 583 | — | 25,900 | — |
| sodium hypochlorite | 0.125 | 242 | 55 | 25,100 | 3 |
|  | 0.25 | 16 | 97 | 25,900 | 0 |
|  | 0.40 | 11 | 98 | 24,600 | 5 |

[1],[2]Amylase and protease were determined by the methods reported in the Food Chemicals Codex, First Supplement: Second Edition, pages 66 and 89 respectively.

EXAMPLE 2

The process of Example 1 was repeated except than the ion salt used was sodium chlorate or sodium perchlorate. The salts were used in the amounts, respectively, of from 0.179% to 2.29% and from 0.236% to 3.02% by weight of the room dry enzyme powder. These amounts of sodium chlorate and sodium perchlorate are the approximate molar equivalents of sodium hypochlorite concentrations of from 0.125% to 1.6%. Neither of these salts had any effect on the protease or amylase activity despite the fact that sodium chlorate and sodium perchlorate are both closely related to chlorite and hypochlorite. This highlights the highly selective and unexpected behavior of the hypochlorite and chlorite ions of the invention in selectively inactivating the amylase.

EXAMPLE 3

Chlorine gas was bubbled at room temperature through 25 g. of the enzyme solution described in Example 1 above. Both protease and amylase were completely inactivated. Chlorine is a well known bleaching agent. Yet it surprisingly fails to achieve the selective amylase inactivation obtainable with the hypochlorite and chlorite ions of the invention.

EXAMPLE 4

An enzyme solution was prepared as in Example 1 and adjusted to pH 6.4. Sodium hypochlorite was added to 976 g. of the pH adjusted solution to obtain a concentration of 0.3% sodium hypochlorite based on the weight of the enzyme composition. The total weight was made up to 1000 g. with tap water. The final pH was 6.5. This procedure was then repeated except that hydrogen peroxide was added to obtain a concentration of 0.15% based on the weight of the enzyme composition. The pH was 6.4. This concentration of hydrogen peroxide is 9.5% greater than an amount equimolar to that of the sodium hypochlorite used at 0.3% concentration. The remainder of the treatment is as described in Example 1. The protease and amylase activities are reported in Table II.

TABLE II
COMPARISON OF THE EFFECT OF HYDROGEN PEROXIDE AND HYPOCHLORITE ON PROTEASE - AMYLASE MIXTURES

| Oxidizing Agent | Amylase Activity | Protease Activity |
|---|---|---|
| sodium hypochlorite | 3 | 27,365 |
| hydrogen peroxide | 236 | 29,579 |

TABLE III
ASSAY OF SPRAY - DRIED PRODUCT

| Oxidizing Agent | Amylase Activity | Protease Activity |
|---|---|---|
| sodium hypochlorite | 15 | 147,650 |
| hydrogen peroxide | 1250 | 157,512 |

The data of Tables II and III demonstrate that hydrogen peroxide, a well-known oxidizing agent, is substantially less effective in selectively inactivating amylase than the hypochlorite of the invention.

EXAMPLE 5

Pancreatin obtained from the Cudahy Co. was dissolved in isotonic salt solution (0.9% NaCl) to a concentration of 3.13 g. in 25 g. of solution. The solution pH was 6.5. Sodium hypochlorite solution (Clorox ®) was added and the increments equalized by the addition of isotonic salt solution. The isotonic salt solution is used to avoid potency degradation of the solution upon standing. The salt has no effect on the differential inactivation set forth in Table IV. A similar lack of effect was noted when using an enzyme solution having a pH of 5.8 rather than 6.5. The enzyme mixture was treated for 1¼ hr. at room temperature and then assayed for protease and amylase activity. As in the prior Examples, the percent sodium hypochlorite is based on the solids content of the enzyme solution. Results are given in Table IV.

TABLE IV

EFFECT OF HYPOCHLORITE ADDITION ON PANCREATIN

| % Sodium Hypochlorite | Amylase Activity[1] | % loss | Protease Activity[2] | % loss |
|---|---|---|---|---|
| 0 | 1075 | — | 27,300 | — |
| 1.8 | 467 | 57 | 28,400 | 0 |
| 3.6 | 31 | 97 | 24,800 | 9 |
| 7.2 | 3 | 100 | 19,100 | 30 |
| 10.8 | 0 | 100 | 11,200 | 59 |

[1],[2]Amylase and protease activity were assayed by the same techniques set forth in Table I.

EXAMPLE 6

Twenty five pounds of an unstandarized, dry enzyme mixture, obtained by drying the clarified culture filtrate from the aerobic fermentation of *Bacillus subtilis* in an aqueous nutrient culture medium containing assimilable C, N and mineral salts, and which was determined to contain neutral protease, alkaline protease and amylase, is admixed with one hundred pounds of water at 70°-85° F. and agitated to facilitate solution. The solution is adjusted to pH 6.2-6.6 by slow addition of 20% aqueous NaOH solution. Then, 1.67 pounds of Clorox ® (containing 5.25% NaOCl) is slowly admixed with the foregoing enzyme solution to thereby result in the addition of 0.0877 pounds or 0.35% NaOCl based on the weight of the dry mixture. The NaOCl immediately destroys the amylase and the resulting solution is then spray dried.

Analysis of the enzyme starting material and the final spray dried material by the methods reported in Table I showed that about 98% of the amylase was inactivated while greater than 90% of the protease (both neutral and alkaline) was retained in the final product.

The above examples and other specific information contained herein are for purposes of illustration only, and such alterations and modifications thereof as would be apparent to those skilled in the art are deemed to fall within the scope and spirit of the invention, bearing in mind that the invention is defined only by the claims appended hereto.

I claim:

1. A method of selectively inactivating amylase in a mixture of protease and amylase, comprising contacting the mixture with an oxidizing agent selected from the group consisting of hypochlorite ions, chlorite ions and mixtures thereof in an amount effective to inactivate the amylase to a substantially greater degree than the protease.

2. The method of claim 1 wherein about 0.1% to about 5% of the oxidizing agent by weight of the mixture is used.

3. The method of claim 1 wherein the mixture is obtained from a bacterial source.

4. The method of claim 1 wherein the mixture is obtained from an animal source.

5. The method of claim 2 wherein the oxidizing agent is hypochlorite ion and about 0.2% to about 0.5% of the agent by weight of the mixture is used.

6. The method of claim 2 wherein the oxidizing agent is chlorite ion and about 0.2% to about 2% of the agent by weight of the mixture is used.

7. The method of claim 6 wherein the amount of the oxidizing agent used is effective to inactivate more than about 80% of the amylase activity but less than about 20% of the protease activity.

8. A method of selectively inactivating amylase in an essentially cell-free aqueous solution of protease-amylase mixture comprising contacting the solution with an oxidizing agent selected from the group consisting of hypochlorite ions, chlorite ions in an amount of about 0.1% to 5% by weight of the mixture.

9. The method of claim 8 wherein the hypochlorite or chlorite ions are provided as the alkali metal salts thereof.

10. The method of claim 8 wherein the hypochlorite or chlorite ions are provided as hypochlorous acid or chlorous acid, respectively.

11. The method of claim 8 wherein the mixture is obtained from a species of *Bacillus*.

12. The method of claim 8 wherein the mixture is obtained from pancreas glands.

13. A method of selectively inactivating amylase in a solution of a protease and amylase-containing enzyme composition prepared from a species of *Bacillus*, comprising treating the solution with about 0.2% to about 0.5% by weight of the protein in solution of an oxidizing agent selected from the group consisting of hypochlorite ions and chlorite ions and mixtures thereof.

14. The method of claim 13 wherein the solution has a pH of about 5.8 to about 7.

15. The method of claim 13 wherein the composition is cell-free.

16. The method of claim 13 wherein the solution is spray dried after the amylase has been inactivated.

17. A method of selectively inactivating amylase to a desired degree in an aqueous solution of a mixed protease-amylase composition prepared from *Bacillus subtilis*, or *Bacillus licheniformis*, comprising treating the solution with about 0.2% to about 0.5% of sodium hypochlorite based on the weight of the composition for a time sufficient to inactivate the amylase to a desired degree.

18. In a method for selectively inactivating amylase in a mixture of protease and amylase, the improvement comprising contacting the mixture with an oxidizing agent selected from the group consisting of hypochlorite ions and chlorite ions and mixtures thereof in an amount effective to inactivate the amylase to a substantially greater degree than the protease.

19. A method of selectively inactivating amylase in a mixture consisting essentially of protease and amylase, comprising contacting the mixture with an oxidizing agent selected from the group consisting of hypochlorite ions and chlorite ions and mixtures thereof in an amount effective to inactivate the amylase to a substantially greater degree than the protease.

* * * * *